(12) United States Patent
Reddy et al.

(10) Patent No.: US 8,404,840 B2
(45) Date of Patent: Mar. 26, 2013

(54) PROCESS FOR THE PREPARATION OF ENDOTHELIN RECEPTOR ANTAGONISTS

(75) Inventors: Manne Satyanarayana Reddy, Hyderabad (IN); Chakilam Nagaraju, Hyderabad (IN); Achampeta Kodanda Ramprasad, Hyderabad (IN)

(73) Assignee: MSN Laboratories Limited, Hyderabad, Andhra Pradesh (IL)

( * ) Notice: Subject to any disclaimer, the term of this patent is extended or adjusted under 35 U.S.C. 154(b) by 0 days.

(21) Appl. No.: 13/127,568

(22) PCT Filed: Nov. 4, 2009

(86) PCT No.: PCT/IN2009/000622
§ 371 (c)(1),
(2), (4) Date: May 31, 2011

(87) PCT Pub. No.: WO2010/070658
PCT Pub. Date: Jun. 24, 2010

(65) Prior Publication Data
US 2011/0263854 A1    Oct. 27, 2011

(30) Foreign Application Priority Data

Nov. 5, 2008 (IN) .......................... 2712/CHE/2008
Nov. 5, 2008 (IN) .......................... 2713/CHE/2008
Mar. 31, 2009 (IN) ............................ 742/CHE/2009

(51) Int. Cl.
C07D 239/02    (2006.01)
(52) U.S. Cl. .......................... 544/302; 544/310; 560/57
(58) Field of Classification Search .................. 544/302, 544/310; 560/57
See application file for complete search history.

(56) References Cited

U.S. PATENT DOCUMENTS 5,932,730 A * 8/1999 Riechers et al. .............. 544/298
2008/0262006 A1* 10/2008 Harbeson ...................... 514/274

FOREIGN PATENT DOCUMENTS

WO    WO 2008/097468 A2    8/2008
WO    WO 2008/097468 A3    8/2008

OTHER PUBLICATIONS

Sorbera, L.A. and Castaner, J. (Drugs of the Future 2005, 30(8):765.*
Amberg et al. (J. Med. Chme 1999, 42, 3026-3032.*
Jansen et al. (Organic Process Research and Development 2001, 5, 16-22.*

(Continued)

*Primary Examiner* — Yong Chu
*Assistant Examiner* — Valerie Rodriguez-Garcia
(74) *Attorney, Agent, or Firm* — Hamilton, Brook, Smith & Reynolds, P.C.

(57) ABSTRACT

The present invention relates to improved processes for the preparation of endothelin receptor antagonists darusentan and ambrisentan, their salts and intermediates. Processes for the preparation of darusentan and ambrisentan comprise reacting benzophenone with a compound of Formula-3 to provide a compound of Formula-4, which on in-situ treatment with methanol and a suitable acid provides a compound of Formula-5; hydrolyzing the compound of Formula-5 to provide a compound of Formula-6; resolving the compound of Formula-6 to provide a compound of Formula-7; esterifying the compound of Formula-7 to provide a compound of Formula-8; reacting the compound of Formula-8 with a compound of Formula-9 to provide a compound of Formula-10; hydrolyzing the compound of Formula-10 to provide darusentan or ambrisentan; and purifiying darusentan or ambrisentan to provide darusentan or ambrisentan having purity greater than 99.00% by HPLC.

10 Claims, 3 Drawing Sheets

OTHER PUBLICATIONS

Written Opinion of the International Preliminary Examining Authority from counterpart International Application No. PCT/IN2009/000622, dated Apr. 8, 2011.

International Preliminary Report on Patentability for PCT/IN2009/000622, dated May 10, 2011.

Author Unknown, "Ambrisentan Treatment of Pulmonary Arterial Hypertension Endothelin $ET_A$ Receptor Antagonist", *Drugs of the Future*, 30(8): 765-770 (2005).

Amberg, W., et al., "Discovery and Synthesis of (S)-3-[2-(3,4-Dimethoxyphenyl) ethoxyl]-2-(4,6-dimethylprimidin-2-yloxy)-3,3-diphenlypropionic Acid (LU 302872), a Novel Orally Active Mixed $ET_A$/ $ET_b$ Receptor Antagonist", *J. Med. Chem.*, 42: 3026-3032 (1999).

Jansen, R., et al., "Structural Similarity and Its Surprises: Endothelin Receptor Antagonists—Process Research and Development Report", *Organic Process Research & Development*, 5: 16-22 (2001).

Riechers, H., et al., "Discovery and Optimization of a Novel Class of Orally Active Nonpeptidic Endothelin-A Receptor Antagonists", *J. Med. Chem.*, 39: 2123-2128 (1996).

International Search Report from counterpart International Application No. PCT/IN2009/000622, dated Apr. 8, 2011.

Author Unknown, "Process for the Production of Ambrisentan", *Research Disclosure Journal*, ISSN 0374-4353, 2 pgs. (Oct. 2008).

* cited by examiner

PROCESS FOR THE PREPARATION OF ENDOTHELIN RECEPTOR ANTAGONISTS

RELATED APPLICATIONS

This application is the U.S. National Stage of International Application No. PCT/IN2009/000622, filed Nov. 4, 2009, which designates the U.S., published in English, and claims priority under 35 U.S.C. §§119 or 365(c) to IN Application No. 2713/CHE/2008, filed Nov. 5, 2008, IN Application No. 2712/CHE/2008, filed Nov. 5, 2008 and IN Application No. 742/CHE/2009, filed Mar. 31, 2009. The entire teachings of the above applications are incorporated herein by reference.

FIELD OF THE INVENTION

The present invention relates to improved processes for the preparation of compounds having the following general formula-1

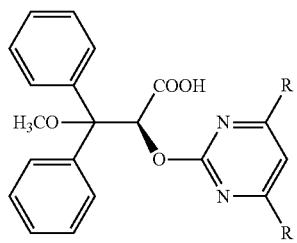

Formula -1

Wherein in R is methyl or methoxy group;

The compound of general formula-1 belongs to a group of drugs known as Endothelin Receptor Antagonists. Endothelin-1 (ET-1) is a 21 amino acid peptide that is produced by the vascular endothelium. It is a very potent vasoconstrictor that binds to smooth muscle endothelin receptors, of which there are two subtypes: $ET_A$ and $ET_B$ receptors. These receptors are coupled to a Gq-protein and receptor activation leads to the formation of $IP_3$, which causes the release of calcium by the sarcoplasmic reticulum (SR) and increased smooth muscle contraction and vasoconstriction.

Ambrisentan is chemically known as (+)-(2S)-2-[(4,6-dimethylpyrimidin-2-yl)oxy]-3-methoxy-3,3-diphenylpropanoic acid (wherein R is methyl group in formula-1) and Darusentan is chemically known as (+)-(2S)-2-[(4,6-dimethoxypyrimidin-2-yl)oxy]-3-methoxy-3,3-diphenylpropanoic acid (wherein R is methoxy group in formula-1) belongs to the group of Endothelin receptor antagonist. Ambrisentan is approved in U.S. for the treatment of pulmonary hypertension and marketed under the brand name LETAIRIS.

BACKGROUND OF THE INVENTION

Ambrisentan and its analogue and their pharmaceutically acceptable salts were disclosed in U.S. Pat. No. 5,932,730. The disclosed process comprises of reacting benzophenone with methyl chloroacetate in presence of sodium methoxide in tetrahydrofuran providing 3,3-diphenyl oxirane-2-carboxylic acid methyl ester, which on in-situ treatment with methanol and $BF_3/Et_2O$ in diethyl ether provides 2-hydroxy-3-methoxy-3,3-diphenylpropionic acid methyl ester. Thus obtained methyl ester is hydrolyzed and then resolved with L-proline methyl ester to provide (S)-2-hydroxy-3-methoxy-3,3-diphenylpropionic acid. The conversion of this intermediate into ambrisentan is not disclosed.

The drugs of future 2005, 30(8), 765-770 disclosed the preparation of racemic ambrisentan. The racemic ambrisentan obtained is converted into active compound by resolving with chiral amine. But the experimental details were not disclosed for the same.

An article published in 'Research Disclosure' disclosed a process which comprises of the condensation of (S)-2-hydroxy-3-methoxy-3,3-diphenyl propionic acid and 4,6-dimethyl-2-(methylsulfonyl)pyrimidine using lithium amide in dimethyl formamide, followed by extraction of the reaction mixture with tertiary butyl ether. The ether layer is concentrated and ambrisentan was isolated by the addition petroleum ether. The usage of ether solvents is commercially not recommendable.

Organic Process Research & Development 2001, 5, 16-22 and J. Med. Chem, 1999, 41, 3026-3032 disclosed a process for the preparation of (S)-2-hydroxy-3-methoxy-3,3-diphenylpropionic acid methyl ester, a key intermediate by esterification of its acid to provide the ester as a crude oil. Repeated the same reactions using high pure (S)-2-hydroxy-3-methoxy-3,3-diphenylpropionic acid only provided ester of maximum 60% purity. Hence when the ester intermediate was used for the preparation of Endothelin receptor antagonists, it provided the products with low yield and high levels of impurity.

Hence the focus of the invention was to prepare (S)-2-hydroxy-3-methoxy-3,3-diphenylpropionic acid methyl ester of high purity, so that it could be used to prepare Endothelin receptor antagonists with substantially high yields and also in a quality which could meet the specifications set by of ICH.

(S)-2-hydroxy-3-methoxy-3,3-diphenylpropionic acid methyl ester has been reported as an oil. In the present invention it was isolated as a crystalline solid which not only improved the yields but also its quality. This when used in the subsequent stages provided the Endothelin receptor antagonists compound in high yields and of high purity.

The discovery of new polymorphic forms of pharmaceutically useful compounds provides a new opportunity to improve the performance characteristics of a pharmaceutical product. There is a need in the art for the preparation of new polymorphic form of Endothelin receptor antagonists, its intermediates and their salts.

The aim of the present invention is to overcome the drawbacks of prior art and to provide an improved process for the preparation of high pure Endothelin Receptor Antagonists and their intermediates such as (S)-2-hydroxy-3-methoxy-3,3-diphenylpropionic acid methyl ester, its salts as well as their crystalline forms.

BRIEF DESCRIPTION OF THE INVENTION

The first aspect of the present invention is to provide an improved process for the preparation of Endothelin receptor antagonists compound of general formula-1, which comprises of the following steps:

a) reacting the benzophenone, compound of formula-2 with alkyl chloroacetate compound of formula-3 in presence of a suitable base in a suitable solvent to provide 3,3-diphenyloxirane-2-carboxylic acid alkyl ester compound of formula-4, which is reacted in-situ with methanol in presence of a suitable acid provides 2-hydroxy-3-methoxy-3,3-diphenylpropionic acid alkyl ester compound of formula-5, b) hydrolyzing the alkyl ester compound of formula-5 with a suitable base in a suitable solvent provides the 2-hydroxy-3-methoxy-3,3-diphenylpropionic acid compound of formula-6, c) resolving the acid compound of formula-6 with a suitable resolving agent in a suitable solvent provides (S)-2-hydroxy-3-methoxy-3,3-diphenylpropionic acid compound of formula-7, d) reacting the compound of formula-7 with a suitable alcohol in presence of a suitable acid catalyst followed by isolation of (S)-2-hydroxy-3-methoxy-3,3-diphenylpropionic acid alkyl ester compound of formula-8 in a suitable hydrocarbon solvents, e) purifying the alkyl ester compound of formula-8 using suitable alcoholic solvents, f) reacting the alkyl ester compound of formula-8 with 4,6-disubstituted-2-(methylsulphonyl)pyrimidine compound of general formula-9 in presence of a suitable base in a suitable solvent provides the ester compound of general formula-10, g) hydrolyzing the ester compound of general formula-10 in presence of a suitable aqueous base in a suitable solvent, followed by isolation of compound of general formula-1, in a suitable solvent, h) purifying the compound of formula-1 in a suitable solvent provides the pure endothelin receptor antagonists compound of general formula-1.

The second aspect of the present invention is to provide an improved process for the preparation of ambrisentan compound of formula-1a, which comprises of reacting the (S)-2-hydroxy-3-methoxy-3,3-diphenylpropionic acid compound of formula-7 with 4,6-dimethyl-2-(methylsulphonyl)pyrimidine compound of formula-9a in the presence of a suitable base in a suitable solvent to provide ambrisentan compound of formula-1a.

The third aspect of the present invention is to provide a process for the purification of compound of general formula-1, which comprises of crystallizing compound of general formula-1 from a solvent selected from the group comprising of alcohol or a polar solvent or mixtures thereof.

The fourth aspect of the present invention is to provide a novel crystalline form of ambrisentan as well as process for its preparation. The novel crystalline form of the present invention is characterized by its PXRD pattern and IR spectrum.

The fifth aspect of the present invention is to provide a novel crystalline form of (+)-(2S)-2-[(4,6-dimethoxypyrimidin-2-yl)oxy]-3-methoxy-3,3-diphenyl propanoic acid compound of formula-1b as well as process for its preparation. The novel crystalline form of the present invention is characterized by its PXRD pattern and IR spectrum.

The sixth aspect of the present invention is to provide an improved process for the preparation of (S)-2-hydroxy-3-methoxy-3,3-diphenylpropionic acid alkyl ester compound of formula-8, which comprises of reacting the (S)-2-hydroxy-3-methoxy-3,3-diphenylpropionic acid compound of formula-7 with suitable alcohol, in presence of a suitable acid catalyst in a suitable solvent, followed by crystallization from suitable hydrocarbon solvents.

The seventh aspect of the present invention is to provide (S)-2-hydroxy-3-methoxy-3,3-diphenylpropionic acid methyl ester compound of formula-8a as a solid. The present invention also provides a novel crystalline form of (S)-2-hydroxy-3-methoxy-3,3-diphenylpropionic acid methyl ester compound of formula-8a and its preparation. The novel crystalline form of (S)-2-hydroxy-3-methoxy-3,3-diphenylpropionic acid methyl ester is characterized by its PXRD, IR and DSC thermogram.

The eighth aspect of the present invention is to provide novel amines salts of (S)-2-hydroxy-3-methoxy-3,3-diphenylpropionic acid compound of general formula-11.

The ninth aspect of the present invention is to provide novel amine salts of ambrisentan compound of general formula-12.

The tenth aspect of the present invention is to provide an improved process for the preparation of (S)-2-hydroxy-3-methoxy-3,3-diphenylpropionic acid compound of formula-7, which comprises of the following steps;

a) treating the 2-hydroxy-3-methoxy-3,3-diphenylpropionic acid compound of formula-6 with R(+)-phenyl ethyl amine in a suitable solvent to provide the (S)-2-hydroxy-3-methoxy-3,3-diphenylpropionic acid R(+)-phenyl ethyl amine compound of formula-11a, b) treating the amine salt compound of formula-11a with a suitable acid in a suitable solvent to provide the compound of formula-7.

ADVANTAGES OF THE PRESENT INVENTION

Provides a commercially viable and eco friendly process for the preparation of Endothelin receptor antagonists compounds of general formula-1 and their intermediates.

Provides highly pure (S)-2-hydroxy-3-methoxy-3,3-diphenylpropionic acid methyl ester & its crystalline forms.

Provides a novel crystalline form of Endothelin receptor antagonists compound of general formula-1.

Avoids the usage of ether solvents in the isolation steps.

Provides highly pure ambrisentan and darusentan.

DETAILED DESCRIPTION OF THE INVENTION

Figure 1:
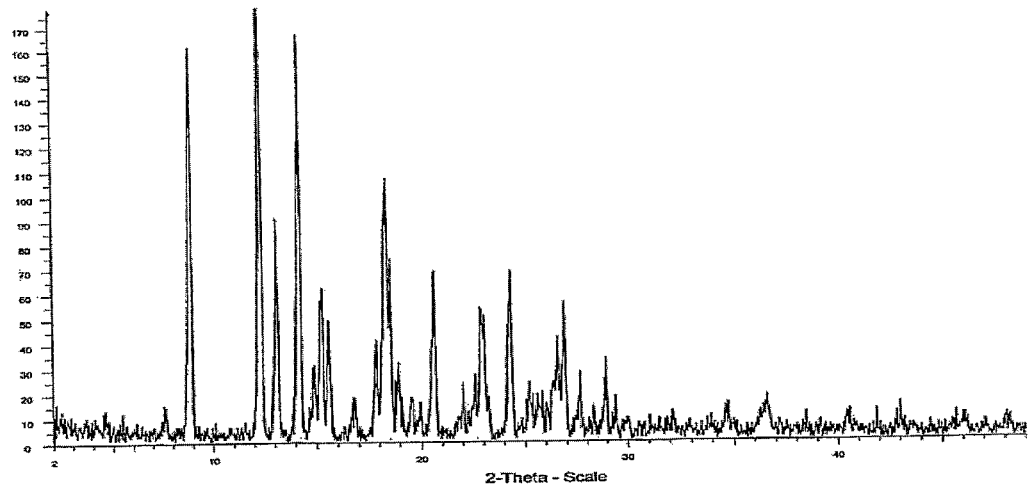
FIG. 1: Illustrates the powder X-ray diffraction pattern of crystalline form-M of ambrisentan

As used herein, the term "Endothelin receptor Antagonist" refers to ambrisentan, which is chemically known as (+)-(2S)-2-[(4,6-dimethylpyrimidin-2-yl)oxy]-3-methoxy-3,3-diphenylpropanoic acid (if R is methyl in formula-1) and darusentan, which is chemically known as (+)-(2S)-2-[(4,6-dimethoxypyrimidin-2-yl)oxy]-3-methoxy-3,3-diphenyl propanoic acid (if R is methoxy in formula-1) were represented by the following general formula-1.

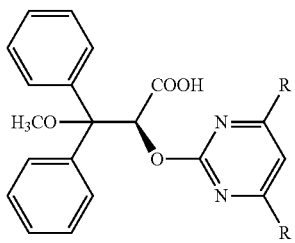

Formula -1

As used herein, the term "lower alkyl" refers to a straight or branched or cyclic $C_1$ to $C_6$ alkyl, including methyl, ethyl, n-propyl, isopropyl, cyclopropyl, n-butyl, isobutyl, sec-butyl, tert-butyl, cyclobutyl, n-pentyl, isopentyl, neopentyl, tert-pentyl, cyclopentyl, n-hexyl, and isohexyl and the like.

As used herein, the term "$C_5$-$C_{10}$ aliphatic hydrocarbon solvents" refers to pentane, hexane, heptane, octane, nonane and decane.

As used herein, the term "alkali metal hydroxide" refers to sodium hydroxide, potassium hydroxide and lithium hydroxide; the term "alkali metal carbonates" refers to sodium carbonate, potassium carbonate, sodium bicarbonate and potassium bicarbonate; the term "alkoxide bases" refers to sodium methoxide, potassium methoxide, sodium tertiary butoxide and potassium tertiary butoxide; the term "alkali metal hydride" refers to sodium hydride, potassium hydride; the term "alkali metal amides" refers to lithium diisopropyl amide, and lithium amide.

As used herein the term "ether solvents" selected from diisopropyl ether, dibutylether, methyl tert-butyl ether, dioxane and tetrahydrofuran; the term "$C_5$-$C_{10}$ aliphatic hydrocarbons" refers to hexane, heptane and the like; the term "aromatic hydrocarbon" refers to toluene, xylene; and cyclohexane; the term "alcohol solvents" refers to methanol, ethanol, isopropanol, 2-butanol; the term "ester solvents" refers to ethyl acetate, methyl acetate and propyl acetate; the term "polar aprotic solvents" refers to dimethyl formamide, dimethylacetamide, dimethyl sulfoxide; the term "ketone solvent" refers to acetone, methyl ethyl ketone, methyl isopropyl ketone and methyl isobutyl ketone; and the term "polar solvent" refers to water.

Accordingly the first aspect of the present invention provides an improved process for the preparation of Endothelin receptor antagonists compound of general formula-1,

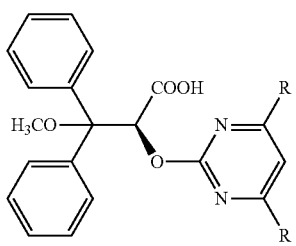

Formula -1

Formula-1a=R=CH$_3$; Formula-1b=R=OCH$_3$
Wherein R is methyl or methoxy group,
which comprises of the following steps;
a) reacting the benzophenone compound of formula-2 with alkyl chloroacetate compound of formula-3 in presence of a suitable base selected from alkali metal hydroxide, alkali metal carbonates, alkoxide bases, preferably alkoxide bases like sodium methoxide in a suitable ether solvents, preferably tetrahydrofuran to provide 3,3-diphenyloxirane-2-carboxylic acid alkyl ester compound of formula-4, which on in-situ treatment with methanol in presence of a suitable acid selected from paratoluene sulfonic acid, hydrochloric acid, oxalic acid and methane sulfonic acid provides the 2-hydroxy-3-methoxy-3,3-diphenylpropionic acid alkyl ester compound of formula-5, b) hydrolyzing the alkyl ester compound of formula-5 with a suitable aqueous alkali metal hydroxides and crystallizing from a suitable solvent selected from $C_5$-$C_{10}$ aliphatic hydrocarbons, aromatic hydrocarbon or mixtures thereof, provides the 2-hydroxy-3-methoxy-3,3-diphenylpropionic acid compound of formula-6, c) resolving the acid compound of formula-6 by treating it with a suitable resolving agent selected from (S)-1-(4-nitrophenyl)ethylamine, R(+)-phenyl ethylamine or L-proline methyl ester or its salts, in a suitable solvent selected from alcohols, ester solvents, ether, solvents or mixtures thereof, followed by crystallization from a suitable solvent selected from $C_5$-$C_{10}$ aliphatic hydrocarbons, aromatic hydrocarbon solvents or mixtures thereof, provides (S)-2-hydroxy-3-methoxy-3,3-diphenylpropionic acid compound of formula-7, d) reacting the compound of formula-7 with suitable alcohol like methanol, ethanol or isopropanol in presence of a suitable catalyst selected from sulphuric acid, hydrochloric acid, thionylchloride, methane sulfonic acid and paratoluene sulfonic acid, followed by isolation in a suitable solvent selected from $C_5$-$C_{10}$ aliphatic hydrocarbons or aromatic hydrocarbon or mixtures thereof, provides the corresponding (S)-2-hydroxy-3-methoxy-3,3-diphenylpropionic acid alkyl ester compound of formula-8, e) purifying the alkyl ester compound of formula-8 using suitable alcoholic solvents or mixtures thereof to provide pure alkyl ester compound of formula-8, f) reacting the pure alkyl ester compound of formula-8 with 4,6-disubstituted-2-(methylsulphonyl)pyrimidine compound of general formula-9

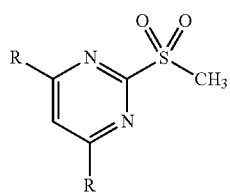

Formula-9

Wherein R is methyl or methoxy;
in presence of a suitable base selected from alkali metal hydride, alkali metal carbonate, alkali metal hydroxide, alkali metal amides, alkoxide, preferably alkali metal carbonates like potassium carbonate in a suitable solvent selected from polar aprotic solvents, ketone solvents or mixture thereof, preferably polar aprotic solvent such as dimethyl formamide provides the ester compound of general formula-10, g) hydrolyzing the ester compound of formula-10 with a suitable aqueous base selected from alkali metal hydroxides, alkali metal carbonates, in a suitable solvent selected from polar solvents, alcohols, ethers or mixture thereof, followed by isolation of compound of general formula-1 in a suitable ester solvent, h) purifying the compound of general formula-1 in a suitable solvent selected from alcoholic solvent or mixtures thereof to provide pure compound of formula-1.

The second aspect of the present invention provides an improved process for the preparation of ambrisentan compound of formula-1a, which comprises of reacting the (S)-2-hydroxy-3-methoxy-3,3-diphenylpropionic acid compound of formula-7, with 4,6-dimethyl-2-(methylsulphonyl)pyrimidine compound of formula-9a in presence a suitable base selected from alkali hydroxides like sodium hydroxide, potassium hydroxide, and tert-butoxide like sodium tert-butoxide, potassium tert-butoxide; and LiHMDS, preferably sodium hydroxide in a suitable solvent selected from ether solvents, ester solvents and mixtures thereof, followed by isolation from a suitable aliphatic or aromatic hydrocarbon solvents provides the ambrisentan compound of formula-1a.

The third aspect of the present invention provides a process for the purification of compound of general formula-1, which comprises of the following steps,
a) dissolving the compound formula-1 in a suitable solvent selected from alcohol solvents like methanol, ethanol, isopropanol, 2-butanol and/or water or mixture thereof by heating to reflux,
b) filtering the solution to remove extraneous matter,
c) cooling the reaction mixture to 0-50° C. and stirred,
d) filtering the precipitated solid and washed with suitable solvent selected from alcohol solvents like methanol, ethanol, isopropanol, 2-butanol and/or water or mixture thereof,
e) drying the solid to get corresponding high pure compound of general formula-1.

The Endothelin receptor antagonists prepared as per the above processes having purity greater than 99.00%, preferably >99.50%, more preferably >99.99% by HPLC.

Figure 2:
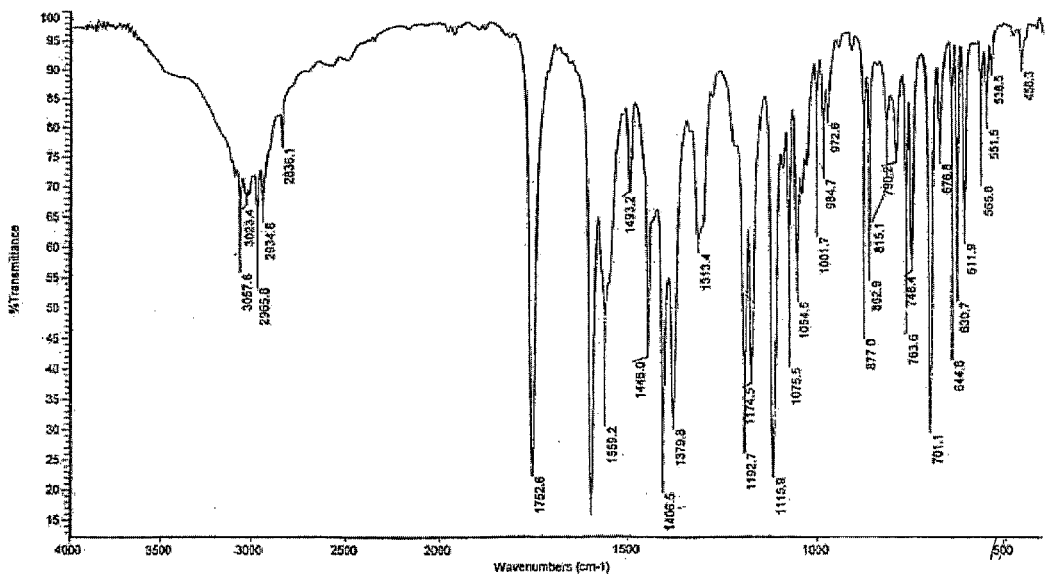
FIG. 2: Illustrates the IR spectrum of crystalline form-M of ambrisentan

The fourth aspect of the present invention provides a novel crystalline form of ambrisentan compound of formula-1a. The novel crystalline form of ambrisentan is herein designated as "Form-M". The novel crystalline form-M of ambrisentan is characterized by its strong X-ray diffractogram having peaks at about 7.54, 8.86, 12.29, 13.06, 14.13, 15.18, 18.2, 20.55, 22.91, 24.26, 26.86, 28.9, 36.54 and 40.45±0.2 degrees two theta as illustrated in FIG. 1. The novel crystalline form-M of ambrisentan is also characterized by its Infrared spectrum having peaks at about 3057.6, 2965.8, 1752.6, 1559.2, 1493.2, 1446.0, 1406.5, 1379.8, 1313.4, 1192.7, 1075.5, 1001.7, 877.0, 701.1 611.9 cm$^{-1}$ as illustrated in FIG. 2.

The present invention also provides a process for the preparation of crystalline form-M of ambrisentan, which comprises of the following steps;
a) dissolving ambrisentan compound of formula-1a in a suitable alcoholic solvent like methanol, ethanol, isopropanol and 2-butanol and/or water or mixtures thereof at reflux temperature,
b) stirring the reaction mixture at reflux,
c) cooling the reaction mixture to 0-50° C.,
d) filtering the precipitated solid and washing with suitable alcoholic solvent like methanol, ethanol, isopropanol and 2-butanol and/or water or mixtures thereof,
e) drying the solid to get the crystalline form-M of ambrisentan.

The fifth aspect of the present invention is to provide a novel crystalline form of. (+)-(2S)-2-[(4,6-dimethoxypyrimidin-2-yl)-oxy]-3-methoxy-3,3-diphenyl propanoic acid compound of formula-1b, herein designated as "Form-M".

Figure 6:
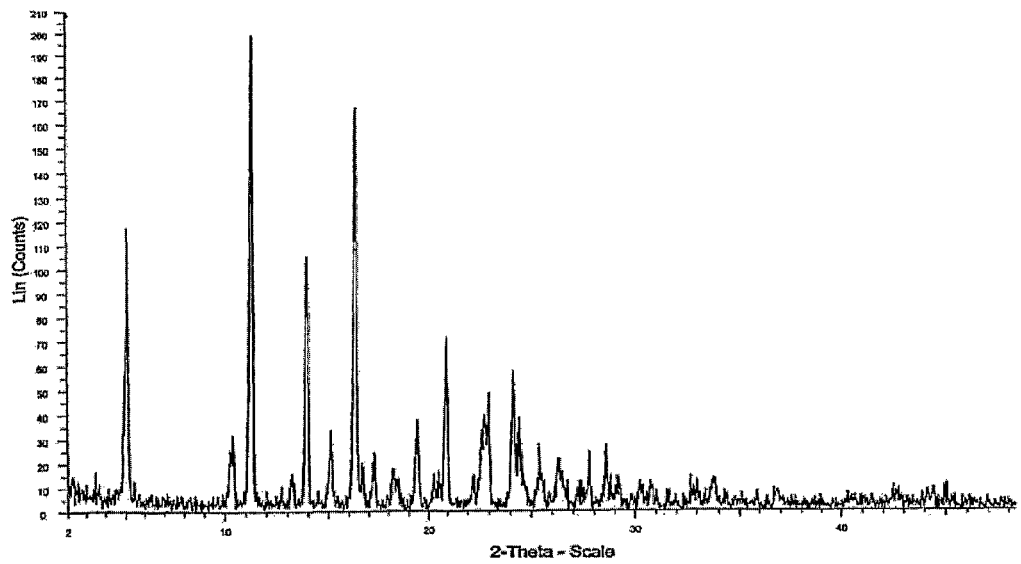
FIG. 6: Illustrates the powder X-ray diffraction pattern of crystalline form-M of compound of formula-1b
Figure 7:
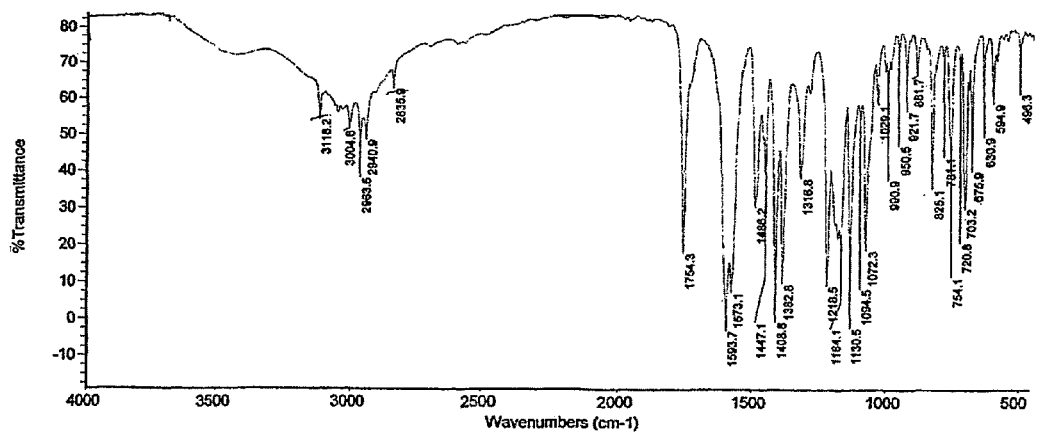
FIG. 7: Illustrates the IR spectrum of crystalline form-M of compound of formula-1b

The novel crystalline form-M of (+)-(2S)-2-[(4,6-dimethoxypyrimidin-2-yl)oxy]-3-methoxy-3,3-diphenyl propanoic acid is characterized by its strong X-ray diffractogram having peaks at about 5.02, 11.25, 13.89, 16.28, 19.3, 20.88, 22.72, 22.86, 24.11, 24.41, 28.54, 30.23 and 33.72±0.2 degrees two theta as illustrated in FIG. 6. The novel crystalline form-M is also characterized by its Infrared spectrum peaks at about 3118.2, 3004.6, 2963.5, 2835.9, 1754.3, 1593.7, 1486.2, 1447.1, 1316.8, 1218.5, 1130.5, 1094.5, 1072.3, 990.9, 825.1, 754.1, 703.2, 630.9 and 594.9 cm$^{-1}$ as illustrated in FIG. 7.

The present invention also provides a process for the preparation of crystalline form-M of (+)-(2S)-2-[(4,6-dimethoxy-pyrimidin-2-yl)oxy]-3-methoxy-3,3-diphenyl propanoic acid, which comprises of the following steps;
a) dissolving (+)-(2S)-2-[(4,6-dimethoxypyrimidin-2-yl)oxy]-3-methoxy-3,3-diphenyl propanoic acid compound of formula-1b in a suitable alcoholic solvent like methanol, ethanol, isopropanol and 2-butanol and/or water or mixtures thereof at reflux temperature,
b) stirring the reaction mixture at reflux,
c) cooling the reaction mixture to 0-50° C.,
d) filtering the precipitated solid and washing with suitable alcoholic solvent like methanol, ethanol, isopropanol and 2-butanol and/or water or mixtures thereof,
e) drying the solid to get the crystalline form-M of (+)-(2S)-2-[(4,6-dimethoxypyrimidin-2-yl)oxy]-3-methoxy-3,3-diphenyl propanoic acid.

The above aspects of the present invention schematically represented as follows:

Scheme-1:

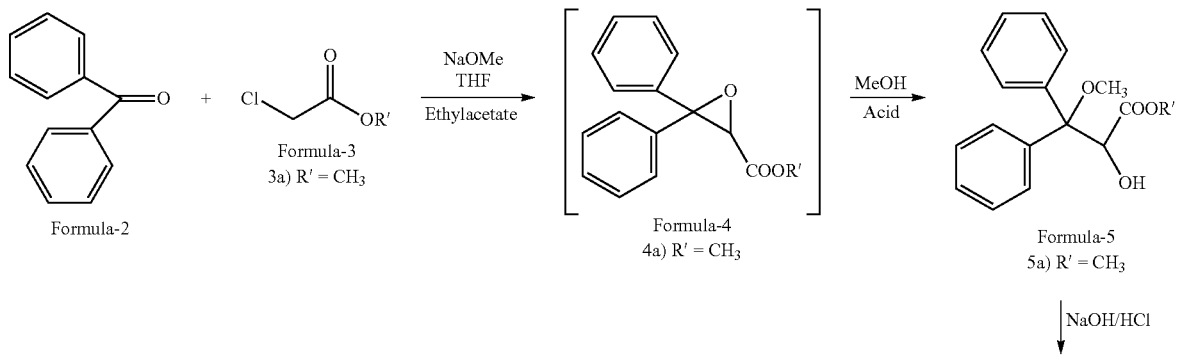

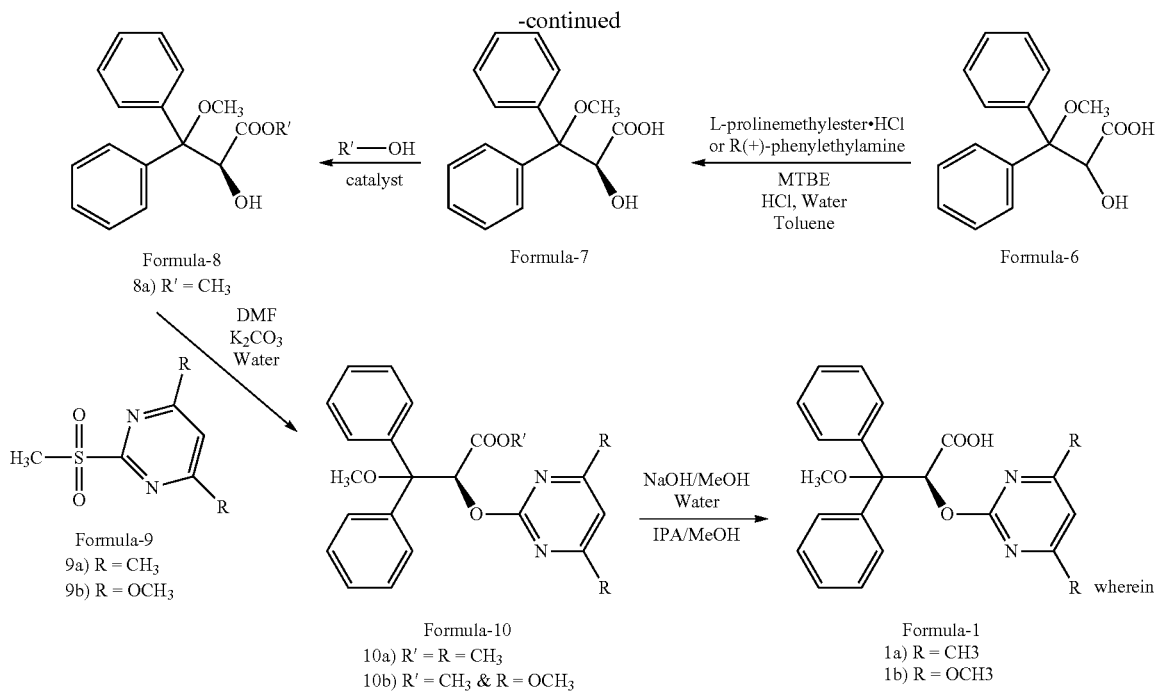

R' is an lower alkyl group which may be a straight or branched or cyclic C1 to C6 alkyl group R is methyl or methoxy group The sixth aspect of the present invention provides a process for the preparation of (S)-2-hydroxy-3-methoxy-3,3-diphenylpropionic acid alkyl ester compound of formula-8, which comprise of the following steps;
a) reacting the acid compound of formula-7 with suitable alcohol selected from methanol, ethanol, isopropanol in presence of a suitable catalyst selected from sulphuric acid, hydrochloric acid, thionylchloride, methane sulfonic acid and paratoluene sulfonic acid,
b) stirring the reaction mixture for sufficient time to complete the reaction,
c) quenching the reaction mixture with water,
d) extracting the reaction mixture into suitable solvent selected from chloro solvent like methylene chloride, chloroform or ester solvent like ethyl acetate, methyl acetate and isopropyl acetate,
e) distilling off the solvent completely under reduced pressure,
f) crystallizing the obtained residue using suitable solvent selected from $C_5$-$C_{10}$ aliphatic hydrocarbon solvents like hexane, heptane; aromatic hydrocarbon solvents like toluene, xylene; and cyclohexane or mixtures thereof provides the compound of formula-8.

The seventh aspect of the present invention provides (S)-2-hydroxy-3-methoxy-3,3-diphenylpropionic acid methyl ester as a solid. The present invention also provides a novel crystalline form of (S)-2-hydroxy-3-methoxy-3,3-diphenylpropionic acid methyl ester compound of formula-8a. This novel crystalline form of formula-8a herein designated as "Form-1".

Figure 3:
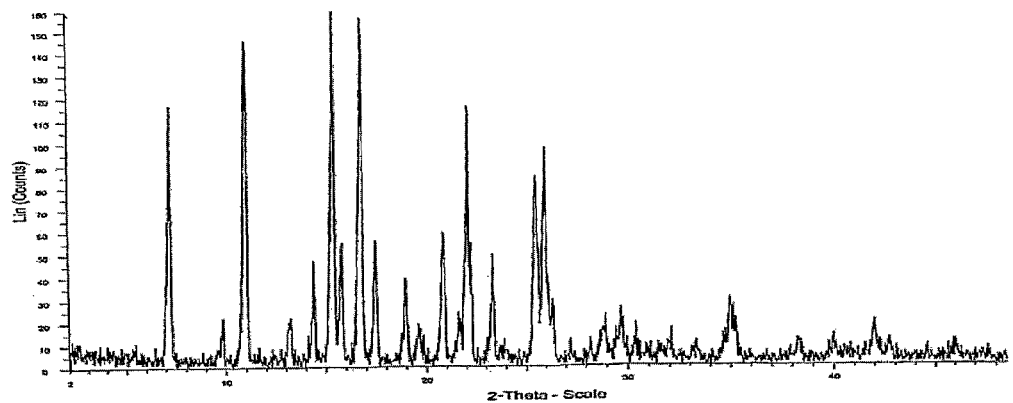
FIG. 3: Illustrates the powder X-ray diffraction pattern of crystalline form-1 of (S)-2-hydroxy-3-methoxy-3,3-diphenylpropionic acid methyl ester
Figure 4:
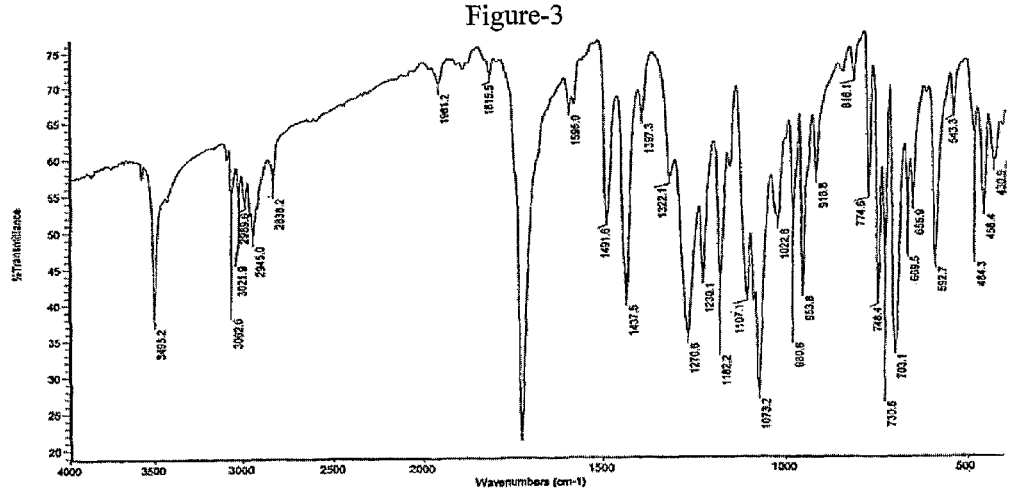
FIG. 4: Illustrates the IR spectrum of crystalline form-1 of (S)-2-hydroxy-3-methoxy-3,3-diphenylpropionic acid methyl ester.
Figure 5:
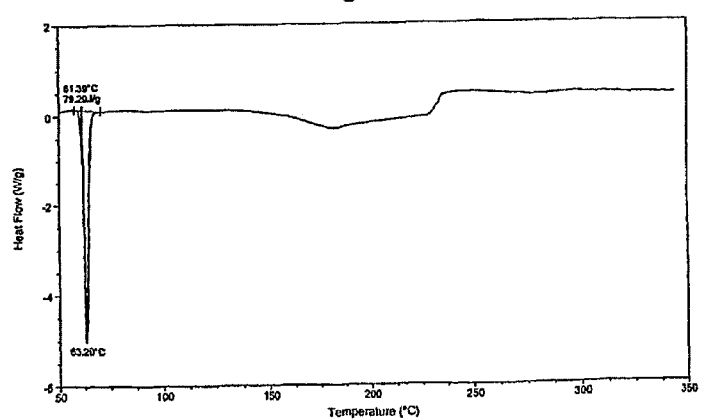
FIG. 5: Illustrates the DSC of crystalline form-1 of (S)-2-hydroxy-3-methoxy-3,3-diphenylpropionic acid methyl ester.

The novel crystalline form-1 of (S)-2-hydroxy-3-methoxy-3,3-diphenylpropionic acid methyl ester compound of formula-8a is characterized by its X-ray diffractogram having peaks at about 7.16, 10.94, 15.31, 15.72, 16.69, 17.42, 20.79, 22.01, 25.42, 25.88, 29.66, 34.98 and 41.96±0.2 degrees two theta as illustrated in FIG. 3. The crystalline form-1 is also characterized by its IR spectrum having peaks at about 3498, 3062, 2945, 1729, 1595, 1491, 1437, 1397, 1491, 1437, 1322, 1270, 1182, 1073, 730, 669 $cm^{-1}$ as illustrate in FIG. 4 and also by DSC thermo gram as illustrated in FIG. 5.

The present invention also provides a process for the preparation of crystalline form-1 of (S)-2-hydroxy-3-methoxy-3,3-diphenylpropionic acid methyl ester compound of formula-8a, which comprises of the following steps;
a) dissolving (S)-2-hydroxy-3-methoxy-3,3-diphenylpropionic acid methyl ester compound of formula-8a in a suitable alcoholic solvent like methanol, ethanol, isopropanol, butanol or mixtures thereof at reflux temperature of the solvent,
b) stirring the reaction mixture for 30 minutes at reflux,
c) cooling the reaction mixture to 10-15° C.,
d) filtering the precipitated solid and washing with suitable alcoholic solvent,
e) drying the solid to get the crystalline form-1 of compound of formula-8a.

The highly pure (S)-2-hydroxy-3-methoxy-3,3-diphenylpropionic acid methyl ester compound of formula-8a used to prepare highly pure Endothelin receptor antagonist compound of general formula-1.

According to the present invention the highly pure compound of formula-8a is having purity grater than 95.00% by HPLC, preferably >98.00%; more preferably 99.50%. The highly pure compound of formula-8a obtained by preparing the compound of formula-8a as per the above process, followed by crystallization in a suitable solvent selected from alcoholic solvent like methanol, ethanol, isopropanol, 2-butanol and polar solvents like water or mixtures thereof.

The eighth aspect of the present invention provides novel amine salts of (S)-2-hydroxy-3-methoxy-3,3-diphenylpropionic acid compounds of general formula-11 having the following structure.

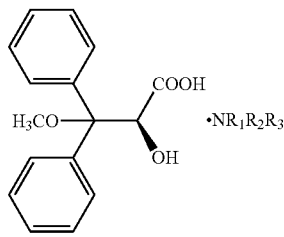

Formula-11

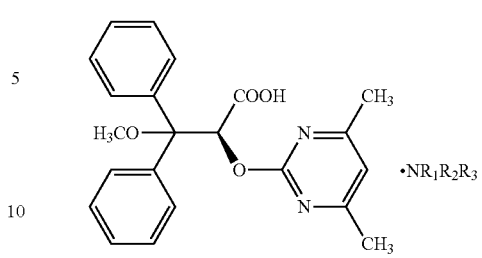

Formula-12

The term "amine salts" of (S)-2-hydroxy-3-methoxy-3,3-diphenylpropionic acid compound of general formula-11 refers to amine salt, in which the amine residue has a formula $NR_1R_2R_3$ wherein $R_1$, $R_2$ and $R_3$ are independently selected from hydrogen, straight or branched chain $C_{1-15}$ alkyl or hydroxyalkyl, $C_{3-10}$ single or fused ring optionally substituted cycloalkyl, independently $R_1$, $R_2$ and $R_3$ can combine with each other to form a $C_{3-7}$ membered cycloalkyl ring or heterocyclic residue containing one or more heteroatom (selected from S, N or O). The amines which are of specific interest are monomethylamine, ethyl amine, n-propylamine, isopropylamine, n-butylamine, 2-butylamine, tertiary butyl amine, cyclohexyl amine, dicyclohexyl amine, benzyl amine, R-phenyl ethyl amine and the like.

The present invention also provides a process for the preparation of novel amine salt compounds of general formula-11, which comprises of reacting the (S)-2-hydroxy-3-methoxy-3,3-diphenylpropionic acid compound of formula-7, with a suitable amine of formula $NR_1R_2R_3$ as defined above, in a suitable solvent selected from a group consisting of but not limited to ether solvents, ester solvents, polar aprotic solvents, ketone solvents, alcoholic solvents, hydrocarbon solvents, chloro solvents, water and mixtures thereof, preferably ester solvent to provide the corresponding amine salt compounds of general formula-11.

The ninth aspect of the present invention provides the novel amine salts of ambrisentan compounds of general formula-12 represented by the following structure.

The term "amine salts" of ambrisentan compounds of general formula-12 of the present invention refers to amine salt, in which the amine residue has a formula $NR_1R_2R_3$, where in $R_1$, $R_2$ and $R_3$ are as defined above for formula-11.

The present invention also provides a process for the preparation of novel ambrisentan amine salt compounds of general formula-12, which comprises of reacting the ambrisentan compound of formula-1a with a suitable amine of formula $NR_1R_2R_3$ as defined above, in a suitable solvent selected from a group consisting of but not limited to ether solvents; ester solvents; polar aprotic solvents; ketone solvents; alcoholic solvents; hydrocarbon solvents; chloro solvents; water and mixtures thereof, preferably ester solvent to provide corresponding amine salt compounds of general formula-12.

The present invention also provides novel amine salts of endothelin receptor antagonists represented by the following structural formula-13,

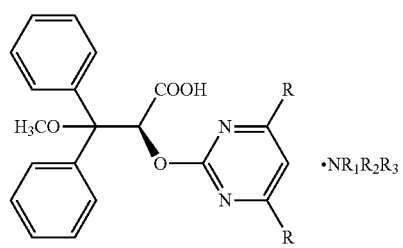

Formula-13

Wherein R is methyl or methoxy group and $NR_1R_2R_3$ is as defined above for formula-12 and are prepared in a similar way as process disclosed in ninth aspect of the present invention using a suitable solvent and amine.

The novel amine salt compounds of general formula-11 & 12 & 13 of the present invention are used to prepare highly pure Endothelin receptor antagonists and their intermediates.

The present aspects of the invention are schematically represented as follows:

Scheme-2:

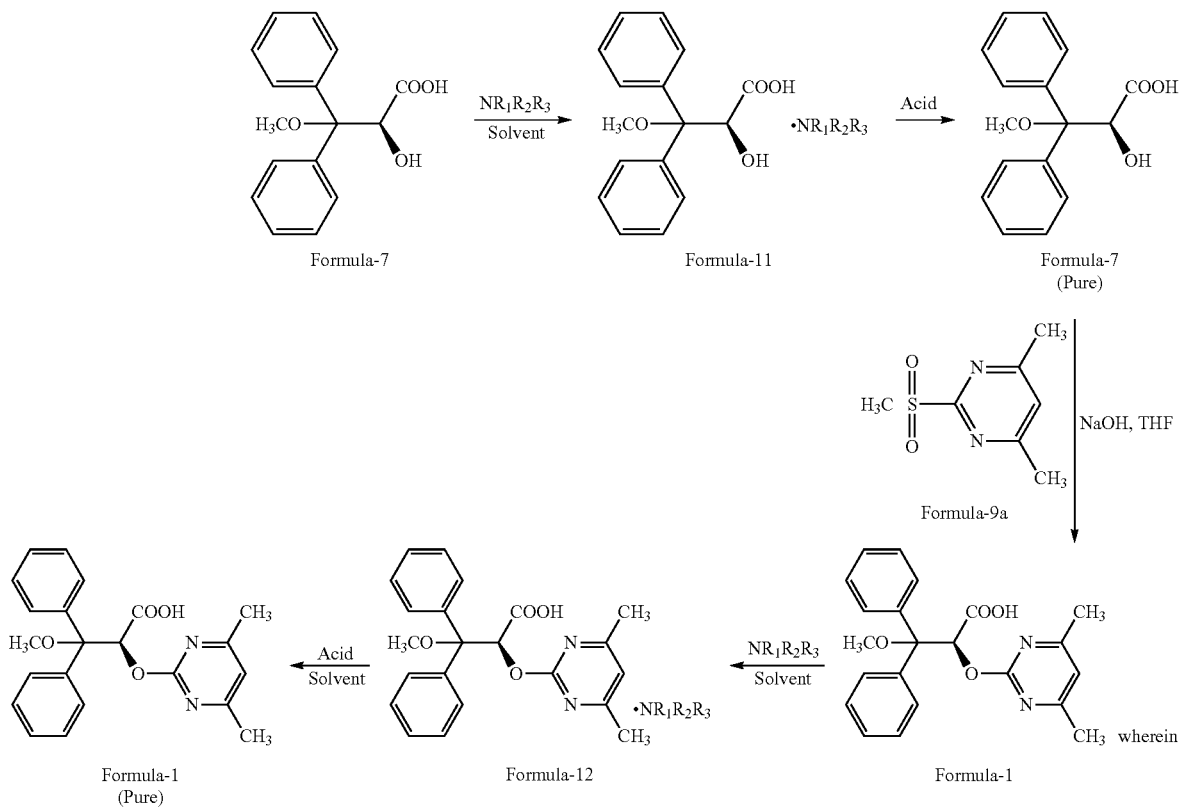

$R_1$, $R_2$ and $R_3$ may be hydrogen or an lower alkyl group which may be a straight or branched or cyclic C1 to C6 alkyl group The tenth aspect of the present invention provides a process for the preparation of (S)-2-hydroxy-3-methoxy-3,3-diphenylpropionic acid compound of formula-7, which comprises of treating the racemic 2-hydroxy-3-methoxy-3,3-diphenylpropionic acid compound of formula-6 with R(+)-phenyl ethyl amine in a suitable solvent selected from a group consisting of but not limited to ether solvents, ester solvents, polar aprotic solvents, ketone solvents, alcoholic solvents, hydrocarbon solvents, chloro solvents; water and mixtures thereof, preferably chloro solvent to provide the R(+)-phenyl ethyl amine salt of (S)-2-hydroxy-3-methoxy-3,3-diphenylpropionic acid compound of formula-11a, Treating the phenyl ethyl amine salt compound of formula-11a with a suitable inorganic acid or organic acid in a suitable solvent selected from ether solvents; ester solvents; polar aprotic solvents; ketone solvents; alcoholic solvents; hydrocarbon solvents; chloro solvents; water and mixtures thereof, preferably ester solvent or in combination with water, to provide the compound of formula-7.

Endothelin receptor antagonists such as ambrisentan and darusentan as well as their pharmaceutically acceptable salts were milled or milled as per the conventional methods to get the desired particle size used as required for preparing pharmaceutical composition and other formulation requirements.

XRD analysis of Endothelin receptor antagonists and its intermediates was carried out using SIEMENS/D-5000 X-Ray diffractometer using Cu, Ka radiation of wavelength 1.54 A° and continuous scan speed of 0.045°/min. FI-IR spectrum of ambrisentan was recorded on Thermo model Nicolet-380 as KBr pellet. The thermal analysis of ambrisentan was carried out on Waters DSCQ-10 model differential scanning calorimeter.

The related substance of ambrisentan, intermediates and its analogue compounds were analyzed by HPLC using the following conditions: Column: symmetry-C18 150×2.1 mm; Flow rate: 0.8 ml/min; wavelength: PDA; Temperature: 25° C.; Load: 20 µl; Run time: 45 min; and using 0.02M potassium dihydrogen orthophosphate and acetonitrile in the ration 1:1 as diluent.

The process described in the present invention was demonstrated in examples illustrated below. These examples are provided as illustration only and therefore should not be construed as limitation of the scope of the invention.

EXAMPLES

Example-1

Preparation of
2-hydroxy-3-methoxy-3,3-diphenylpropionic acid
methyl ester compound of formula-5a Mixture of benzophenone (100 grams) and methyl chloroacetate (84 grams) in tetrahydrofuran (160 ml) was added to a cooled mixture of tertrahydrofuran and sodium methoxide (51.8 grams) at below −4° C. in 90 minutes, stirred for 30 minutes at −10° C. to −5° C. The reaction mixture temperature was raised to 25-35° C., quenched with water and then extracted with ethyl acetate. The organic layer was washed with brine solution and dried over sodium sulphate. The organic layer was distilled under reduced pressure at 60° C. and methanol was added to the obtained residue then methanol was distilled off completely. The reaction mixture cooled to 25-35° C. and methanol (280 ml) was added to it. Paratoluene sulfonic acid (4 grams) was added to the above reaction mixture. The reaction mixture was stirred for 2 hours at 25-35° C. and then cooled to 0-5° C. and stirred 45 minutes. The obtained solid was filtered, washed with methanol and then dried at 50-60° C. to get the title compound.

Yield: 110 grams; M.R: 92-96° C.

Example-2

Preparation of
2-hydroxy-3-methoxy-3,3-diphenylpropionic acid
compound of formula-6

Mixture of 2-hydroxy-3-methoxy-3,3-diphenylpropionic acid methyl ester (100 grams) and aqueous sodium hydroxide solution (22 grams in 200 ml of water) was heated to 95-100° C. and stirred for 120 minutes. The reaction mixture was cooled to 40-45° C. and quenched with water. The pH of the reaction mixture was adjusted to 1.3 with concentrated hydrochloric acid and extracted with ethyl acetate. The solvent from the ethyl acetate layer was distilled off completely under reduced pressure at 60° C. The reaction mixture was cooled to 40° C. and cyclohexane (230 ml) was added and stirred at reflux for 30 minutes. The reaction mixture was cooled to 25-35° C. and stirred for 40 minutes at 25-35° C. The solid formed was filtered off and washed with cyclohexane then dried at 60-70° C. to get the title compound.

Yield: 92 grams; M.R: 108-112° C.

Example-3

Preparation of
(S)-2-hydroxy-3-methoxy-3,3-diphenylpropionic
acid compound of formula-7

Methanolic sodium methoxide solution (33 grams) was added to the solution of L-proline methyl ester hydrochloride (30.38 grams) in methanol (28 ml), stirred for 15 minutes at 25-35° C. then filtered to remove the unwanted solid. The solvent from the reaction mixture was distilled off under reduced pressure at 60° C. The solution of 2-hydroxy-3-methoxy-3,3-diphenylpropionic acid compound of formula-6 (50 grams) in methyltertiarybutylether (530 ml) was added to the above residue. The reaction mixture was heated to reflux temperature (55-60° C.), stirred for 45 minutes and then cooled to 25-35° C. and further stirred for 30 minutes. The solid separated was filtered off and washed with MTBE. Water (220 ml) was added to the filtrate and pH was adjusted to 1.2 with hydrochloric acid. The aqueous and organic layers were separated and then aqueous layer extracted with MTBE. The total organic layer washed with water and then distilled off the solvent completely under reduced pressure at 60° C. Toluene (100 ml) was added to the residue, heated to reflux temperature for 15 minutes then cooled to 25-35° C. and stirred for 45 minutes. The obtained solid was filtered off and washed with toluene then dried at 50-60° C. to get the title compound.

Yield: 17 grams
M.R: 118-122° C.
S.O.R: +26° (C=0.5; MeOH)

Example-4

Preparation of
(S)-2-hydroxy-3-methoxy-3,3-diphenylpropionic
acid compound of formula-7

The title compound is prepared in a similar manner to example-3 using the ethyl acetate as a solvent in place of methyl tertiary butyl ester.

Yield: 16.5 grams
S.O.R: +21° (C=0.5; MeOH)

Example-5

Preparation of
(S)-2-hydroxy-3-methoxy-3,3-diphenylpropionic
acid methyl ester compound of formula-8a Paratoluene sulfonic acid (7.9 grams) was added to a mixture of S-2-hydroxy-3-methoxy-3,3-diphenylpropionic acid compound of formula-7 (50 grams) and methanol (150 ml) at 25-35° C. then stirred for 48 hours at 25-35° C. The reaction mixture was quenched with cooled water (200 ml) and methylene chloride (150 ml) was added to it. The aqueous and organic layers were separated and aqueous layer was extracted with methylene chloride. The organic layer combined, washed with sodium bicarbonate solution and the solvent from the organic layer distilled off under reduced pressure at 55° C. Cyclohexane (50 ml) was added to the residue and stirred at 30 minutes at 45-50° C. The reaction mixture was initially cooled to 25-30° C. and then to −5 to 0° C. The reaction mixture was stirred for 60 minutes at −5 to 0° C. The obtained solid was filtered and washed with chilled cyclohexane. The solid was dried at 25-35° C. to get the title compound. The PXRD, IR and DSC of the obtained solid compound were similar to the crystalline form-I of formula-8a.

Yield: 35 grams; M.R: 58-60° C.
S.O.R: +39.3° (C=0.5; MeOH)
Purity: 98.5% by HPLC Example 6 to 9

Preparation of
(S)-2-hydroxy-3-methoxy-3,3-diphenylpropionic
acid methyl ester compound of formula-8a The title compound (S)-2-hydroxy-3-methoxy-3,3-diphenylpropionic acid methyl ester has been prepared in analogues manner to example-5 using the appropriate amount starting material, methanol and catalyst in the ratio which are mentioned in the following table.

| Example | Formula-7 | Methanol | Acid Catalyst | | Yield |
| --- | --- | --- | --- | --- | --- |
| | | | Acid used | Qty. | |
| 6 | 5 grams | 20 ml | SOCl$_2$ | 0.10 grams | 4.5 grams |
| 7 | 5 grams | 50 ml | H$_2$SO$_4$ | 0.190 grams | 4.5 grams |
| 8 | 40 grams | — | Methanolic HCl | 160.0 ml | 38 grams |
| 9 | 10 grams | 30 ml | Methane sulfonic acid | 0.88 grams | 10 grams |

Example-10

Purification of compound of formula-8a

A mixture of (S)-2-hydroxy-3-methoxy-3,3-diphenylpropionic acid methyl ester (5 grams) and 2-butanol (50 ml) was heated to reflux temperature. The reaction mixture was stirred for 30 minutes at 88-92° C. and then cooled to 10-15° C. The precipitated solid was filtered, washed with 2-butanol and then dried to get the high pure title compound.

Yield: 4.2 grams
Purity: 99.10% by HPLC

Example-11

Preparation of crystalline form-1 of compound of formula-8a

A mixture of (S)-2-hydroxy-3-methoxy-3,3-diphenylpropionic acid methyl ester (5 grams) and isopropyl alcohol (50 ml) was heated to reflux temperature. The reaction mixture was stirred for 30 minutes at 75-80° C. and then cooled to 10-15° C. The precipitated solid was filtered, washed with isopropyl alcohol and then dried to get the high pure title compound.

Yield: 4.0 grams

Example-12

Preparation of (+)-(2S)-2-[(4,6-dimethylpyrimidin-2-yl)oxy]-3-methoxy-3,3-diphenylpropanoic acid methyl ester compound of formula-10a Mixture of (S)-2-hydroxy-3-methoxy-3,3-diphenylpropionic acid methyl ester compound formula-8a (50 grams), dimethyl formamide (500 ml) and potassium carbonate (12 grams) was stirred at 40 minutes at 25-35° C. 4,6-dimethyl-2-(methylsulphonyl)pyrimidine (34.5 grams) was added and heated to 90-95° C. and stirred for 4 hours. The reaction mixture was cooled to 25-35° C. Water (250 ml) was added and stirred for 60 minutes. The solid obtained was filtered, washed with water and then dried at 60-70° C. to get the title compound.

Yield: 55 grams
M.R: 130-140° C.;
S.O.R: +135.8° (C=0.5; MeOH)

Example-13

Preparation of ambrisentan compound of formula-1a

Aqueous sodium hydroxide solution (10 grams in 250 ml of water) was added to the mixture of 1,4-dioxane (500 ml) and (+)-(2S)-2-[(4,6-dimethylpyrimidin-2-yl)oxy]-3-methoxy-3,3-diphenylpropanoic acid methyl ester (50 grams) compound of formula-10a at 25-35° C., then heated to 85-90° C. and stirred for 3 hours. The reaction mixture was cooled to 25-35° C. and water (500 ml) was added. The reaction mixture was washed with ethylacetate. The pH of aqueous layer was adjusted to 1.8 with hydrochloric acid at 25-35° C. The reaction mixture was extracted with ethyl acetate. The ethyl acetate layer was distilled off under reduced pressure at below 60° C. and cooled to 0-5° C. The reaction mixture was stirred for 60 minutes at 0-5° C. The obtained solid was filtered, washed with chilled ethyl acetate and dried at 60-70° C. to get the ambrisentan. Yield: 36 grams

Example-14

Purification of Ambrisentan

Mixture of ambrisentan (30 grams), isopropyl alcohol (189 ml) and methanol (21 ml) was heated to reflux. The reaction mixture was filtered and washed with a mixture of isopropyl alcohol and methanol. The filtrate was cooled to 25-35° C. and stirred for 45 minutes. The solid obtained is filtered, washed with a mixture of isopropyl alcohol and methanol then dried at 60-70° C. to get high pure ambrisentan.

Yield: 22 grams
S.O.R: +183.37° (C=0.5; MeOH)
Purity: 99.92% by HPLC

Example-15

Purification of Ambrisentan

Mixture of ambrisentan (30 grams) and isopropyl alcohol (210 ml) was heated to 80-85° C. The reaction mixture was filtered at 80-85° C. and washed with isopropyl alcohol. The filtrate was cooled to 25-35° C. and stirred for 45 minutes. The solid obtained is filtered, washed with isopropyl alcohol then dried at 60-70° C. to get high pure ambrisentan.

Yield: 21.5 grams
Purity: 99.90% by HPLC.

Example-16

Preparation of (+)-(2S)-2-[(4,6-dimethoxypyrimidin-2-yl)oxy]-3-methoxy-3,3-diphenylpropanoic acid methyl ester compound of formula-10b Mixture of (S)-2-hydroxy-3-methoxy-3,3-diphenylpropionic acid methyl ester compound of formula-8a (50 grams), acetone (500 ml) and potassium carbonate (12 grams) was stirred for 40 minutes at 25-35° C. 4,6-dimethoxy-2-(methylsulphonyl)pyrimidine (29.25 grams) was added to the above reaction mixture, heated to 55-60° C. and stirred for 10 hours. The reaction mixture was cooled to 25-35° C., filtered and washed with acetone. The filtrate was distilled off under reduced pressure at 50° C. The reaction mixture was cooled to 25-35° C. and quenched with water. The reaction mixture was extracted with ethyl acetate. The ethyl acetate layer was distilled off completely under reduced pressure at 60° C. The reaction mixture cooled to 45° C. and methanol was added then distilled off methanol. Methanol (100 ml) was added to the obtained residue and heated to 55-60° C. and stirred for 30 minutes. The reaction mixture was cooled to 20-25° C. and stirred for 45 minutes. The obtained solid was filtered off and washed with methanol. The solid was dried at 50-60° C. to get the title compound.

Yield: 41 grams
M.R: 108-112° C.; S.O.R: +115° (C=0.5; MeOH)

Example-17

Preparation of (+)-(2S)-2-[(4,6-dimethoxypyrimidin-2-yl)oxy]-3-methoxy-3,3-diphenyl propanoic acid compound of formula-1b Aqueous sodium hydroxide (5.59 grams in 75 ml of water) was added to the mixture of (+)-(2S)-2-[(4,6-dimethoxypyrimidin-2-yl)oxy]-3-methoxy-3,3-diphenyl propanoic acid methyl ester (30 grams) and methanol (300 ml) at 25-35° C. The reaction mixture was heated to 55-60° C. and stirred for 3 hours. The solvent from the reaction mixture was distilled off under reduced pressure at 60° C. The reaction mixture was cooled to 25-35° C. and quenched with water. The reaction mixture was washed with ethyl acetate. The pH of aqueous layer was adjusted to 5.8 with aqueous acetic acid and extracted with ethyl acetate. The ethyl acetate was distilled off completely from the reaction mixture under reduced pressure at 60° C. Then the reaction mixture was cooled to 40° C., acetone was added and then distilled off the acetone completely. The obtained residue dissolved in acetone and water (300 ml) was slowly added to it. The reaction mixture was stirred for 45 minutes at 25-35° C. The solid obtained was filtered and washed with water. The solid was dried at 60-70° C. to get the title compound.
Yield: 27 grams;
M.R: 166-170° C.;
S.O.R: +144.0° (C=0.5; MeOH)

Example-18

Purification of (+)-(2S)-2-[(4,6-dimethoxypyrimidin-2-yl)oxy]-3-methoxy-3,3-diphenyl propanoic acid compound of formula-1b A mixture of (+)-(2S)-2-[(4,6-dimethoxypyrimidin-2-yl)oxy]-3-methoxy-3,3-diphenyl propanoic acid (10 grams) and isopropyl alcohol (30 ml) was heated to 80-85° C. temperature. The reaction mixture was filtered at 75-80° C. to remove the extraneous matter. The filtrate was initially cooled to 20-25° C. and then cooled to 0-5° C. The reaction mixture was stirred for 30 minutes at 0-5° C. The precipitated solid was filtered and washed with isopropyl alcohol then dried to get the high pure title compound.
Yield: 6.5 grams:
Purity: 99.96% by HPLC Example-19

Preparation of Ambrisentan Compound of Formula-1a (S)-2-hydroxy-3-methoxy-3,3-diphenylpropionic acid (20 grams in 20 ml of THF) was added to a mixture of sodium hydroxide (8.5 grams) and tetrahydrofuran (110 ml) and stirred for 20 minutes at 25-35° C. 4,6-dimethyl-2-(methylsulphonyl)pyrimidine (19 grams) was added to the reaction mixture and heated to 40-45° C. then stirred for 24 hours. The reaction mixture was cooled to 25-35° C. and quenched with water then washed with cyclohexane. The reaction mixture was acidified with hydrochloric acid and then extracted into ethyl acetate. The combined ethyl acetate layer was washed with sodium chloride solution and then distilled off completely under reduced pressure. The reaction mixture was cooled to 25-35° C., cyclohexane (100 ml) was added to it and then heated to 60-65° C. The reaction mixture was cooled to 25-30° C. and stirred for 45 minutes. The solid obtained was filtered, washed with cyclohexane and then dried to get the title compound.
Yield: 19 grams;
S.O.R: +144.87° (C=0.5 in MeOH)

Example-20

Preparation of Ambrisentan Compound of Formula-1a

The title compound prepared in a similar manner to example-19 except lithium hexamethyldisilazide (115 ml) (20% solution in tetrahydrofuran) was used in the place of sodium hydroxide for 15 grams of (S)-2-hydroxy-3-methoxy-3,3-diphenylpropionic acid and isolating the title compound using ethyl acetate.
Yield: 13.5 grams; S.O.R: +161.07°

Example-21

Preparation of Ambrisentan Compound of Formula-1a

The title compound prepared in a similar manner to example-19 except that the sodium tertiary butoxide (2.2 grams) was used in the place of sodium hydroxide for 5 grams of (S)-2-hydroxy-3-methoxy-3,3-diphenylpropionic acid.
Yield: 2.5 grams
M.R: 188-192° C.

Example-22

Preparation of (S)-2-hydroxy-3-methoxy-3,3-diphenylpropionic acid

R(+)-phenyl ethyl amine (11.12 grams) was added to a solution of 2-hydroxy-3-methoxy-3,3-diphenylpropionic acid (25 grams) and chloroform (25 ml) at 40° C. and stirred for 30 minutes. The reaction mixture was cooled, and the solid obtained was filtered and washed with chloroform. Ethyl acetate (50 ml) and water (50 ml) was added to the obtained solid and then the reaction mixture was acidified with concentrated hydrochloric acid. The layers were separated and the aqueous layer extracted with ethyl acetate. The solvent from combined organic layer was distilled off completely under reduced pressure at below 60° C. The obtained residue was dissolved in toluene (30 ml) at 60-70° C. and then cooled to 25-30° C. The solid was filtered, washed with toluene and then dried to get the title compound.
Yield: 5.5 grams; S.O.R: +28.32°

Example-23

Preparation of (S)-2-hydroxy-3-methoxy-3,3-diphenylpropionic acid

The title compound was prepared in a similar manner to example-4 except that 8.89 grams of R(+)-phenyl ethyl amine was used instead of 11.85 grams of R(+)-phenyl ethylamine.
Yield: 6.0 grams; S.O.R: +27.0°

Example-24

Preparation of tertiary butyl amine salt of (S)-2-hydroxy-3-methoxy-3,3-diphenylpropionic acid A solution of tertiary butyl amine (1.61 grams) in ethyl acetate (5 ml) was added to a solution of (S)-2-hydroxy-3-methoxy-3,3-diphenylpropionic acid (5 grams) in ethyl acetate (20 ml) at 25-30° C. and stirred for 45 minutes. The solid formed was filtered, washed with ethyl acetate and then dried to get the title compound
Yield: 6.5 grams
M.R: 210-216° C.
Purity by HPLC: 99.77%

Example-25-27

Amine salts of (S)-2-hydroxy-3-methoxy-3,3-diphenylpropionic acid

The amine salts of (S)-2-hydroxy-3-methoxy-3,3-diphenylpropionic acid which are mentioned in the following table has been prepared analogues manner to example-24 using the appropriate amount starting material, amine and ethylacetate in the ration which are mentioned in the following table.

| Ex. No | Formula | Amine (Qty.) | Ethyl Acetate | Yield | M.R | Purity |
|---|---|---|---|---|---|---|
| 25 | 10 grams | Monomethyamine (3.46 grams) | 50 ml | 8.5 grams | 196-198° C. | 99.89% |
| 26 | 5 grams | Dicyclohexylamine (3.99 grams) | 25 ml | 7.5 grams | 190-194° C. | |
| 27 | 5 grams | R(+)-phenyl ethylamine (2.6 grams) | 40 ml | 7.0 | 180-184° C. | 99.78% |

Example-28

Preparation of dicyclohexylamine salt of (+)-(2S)-2-[(4,6-dimethylpyrimidin-2-yl)oxy]-3-methoxy-3,3-diphenylpropanoic acid A solution of dicyclohexylamine (2.87 grams) in ethyl acetate was added to a solution of ambrisentan (5 grams) in ethyl acetate (20 ml) at 25-30° C. and stirred for 45 minutes. The solid formed was filtered, washed with ethyl acetate and then dried to get the title compound
Yield: 2 grams;
M.R: 180-184° C.
Purity by HPLC: 99.01%

Example-29 & 30

Monomethylamine & tertiarybutylamine salt of (+)-(2S)-2-[(4,6-dimethyl pyrimidin-2-yl)oxy]-3-methoxy-3,3-diphenylpropanoic acid Monomethylamine & tertiarybutylamine salt was prepared in a similar manner to example-28 using 5 grams of ambrisentan & amount of amine mentioned in the following table as input and the corresponding results are tabulated as follows

| Ex. No | Salt | Qty | Yield | M.R | Purity |
|---|---|---|---|---|---|
| 29 | Monomethyamine | 0.48 | 2.5 | 188-192° C. | 99.00% |
| 30 | Tertiarybutylamine | 1.15 | 5.0 | 198-206° C. | 99.50% |

Example-31

Preparation of (+)-(2S)-2-[(4,6-dimethylpyrimidin-2-yl)oxy]-3-methoxy-3,3-diphenylpropanoic acid from amine salt Monomethyl amine salt of (+)-(2S)-2-[(4,6-dimethylpyrimidin-2-yl)oxy]-3-methoxy-3,3-diphenylpropanoic acid (1.5 grams) was taken in water (6 ml) and acidified it using hydrochloric acid at 25-30° C. The reaction mixture was stirred for 90 minutes at 25-30° C. The solid obtained was filtered, washed with water and then dried to get the title compound.
Yield: 1.2 grams

Example-32

Preparation of (+)-(2S)-2-[(4,6-dimethylpyrimidin-2-yl)oxy]-3-methoxy-3,3-diphenylpropanoic acid Tert-butyl amine salt of (+)-(2S)-2-[(4,6-dimethylpyrimidin-2-yl)oxy]-3-methoxy-3,3-diphenylpropanoic acid (3.0 grams) was taken in water (12 grams) and acidified it using hydrochloric acid. The reaction mixture stirred for 90 minutes at 25-30° C. The solid obtained was filtered, washed with water and then dried to get the title compound.
Yield: 2.6 grams

We claim:

1. A process for the preparation of a compound having the following structural formula:

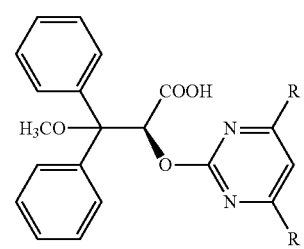

Formula-1 wherein R is methyl or methoxy;
the process comprising:
a) reacting benzophenone with compound of Formula-3,

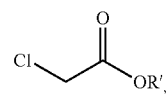

Formula-3 wherein R' is a straight or branched or cyclic C1-C6 alkyl group, in the presence of a base and in a solvent to provide compound of Formula-4,

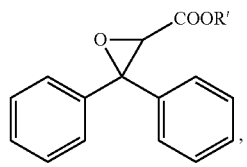

Formula-4 wherein R' is as defined above,
which on in-situ treatment with methanol in presence of a suitable acid provides compound of Formula-5

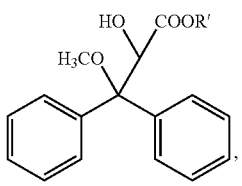

Formula-5 wherein R' is as defined above;

b) hydrolyzing the compound of Formula-5 in presence of a base in a solvent, followed by crystallization from hydrocarbon solvent provides compound of Formula-6

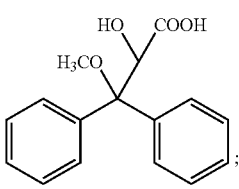

Formula-6 c) resolving the compound of Formula-6 by treating it with a resolving agent in a solvent, followed by crystallization from hydrocarbon solvent provides compound of Formula-7

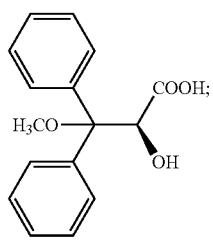

Formula-7 d) reacting the compound of Formula-7 with an amine of formula $NR_1R_2R_3$, wherein:

$R_1$, $R_2$ and $R_3$ are each independently selected from hydrogen, straight or branched-chain C1-C15 alkyl or hydroxyalkyl, and C3-C10 single or fused ring optionally substituted cycloalkyl, or $R_1$, $R_2$ and $R_3$ can combine with each other to form a 3-7-membered heterocyclic ring which, in addition to the nitrogen of $NR_1R_2R_3$ can contain one or more heteroatoms selected from N, S and O, in an ether solvent, ester solvent, polar aprotic solvent, ketone solvent, alcoholic solvent, hydrocarbon solvent, chloro solvent, water, or a mixture thereof, to provide compound of Formula-11

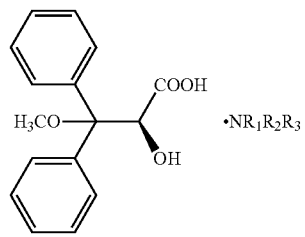

Formula-11 and isolating the compound of Formula-11;

e) reacting the isolated compound of Formula-11 with an inorganic or organic acid in an ether solvent, ester solvent, polar aprotic solvent, ketone solvent, alcoholic solvent, hydrocarbon solvent, chloro solvent, water, or a mixture thereof to provide the compound of Formula-7;

f) treating the compound of Formula-7 from step e) with alcohol of formula R'—OH, wherein R' is defined as above, in presence of an acid catalyst followed by isolation from a hydrocarbon solvent, to provide compound of Formula-8

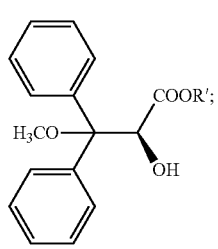

Formula-8 g) crystallizing the compound of Formula-8 using a solvent to provide crystalline compound of Formula-8, h) reacting the crystalline compound of Formula-8 with compound of Formula-9

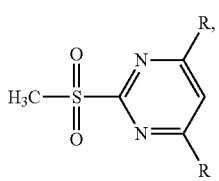

Formula-9 wherein R is defined as above, in presence of a base in a solvent, to provide compound of Formula-10

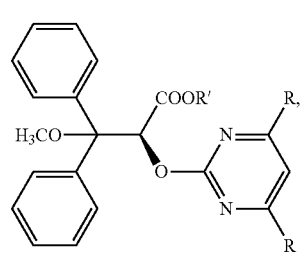

Formula-10 wherein R and R' are defined as above;

i) hydrolyzing the compound of Formula-10 with a base in a solvent followed by isolation from an ester solvent, to provide the compound of Formula-1;

j) reacting the compound of Formula-1 with an amine of formula $NR_{1'}R_{2'}R_{3'}$, wherein $R_{1'}$, $R_{2'}$, and $R_{3'}$ are each independently selected from hydrogen, straight or branched-chain C1-C15 alkyl or hydroxyalkyl, and C3-C10 single or fused ring optionally substituted cycloalkyl, or $R_{1'}$, $R_{2'}$, and $R_{3'}$ can combine with each other to form a 3-7-membered heterocyclic ring which, in addition to the nitrogen of $NR_{1'}R_{2'}R_{3'}$, can contain one or more heteroatoms selected from N, S and O, in an ether solvent, ester solvent, polar aprotic solvent, ketone solvent, alcoholic solvent, hydrocarbon solvent, chloro solvent, water, or a mixture thereof, to provide compound of Formula-13

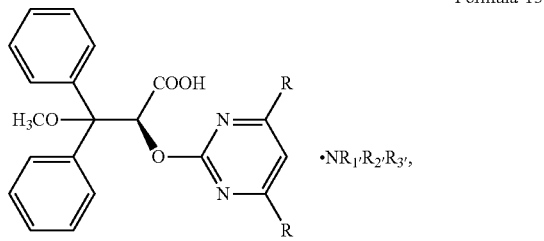

Formula-13 wherein R, $R_{1'}$, $R_{2'}$, and $R_{3'}$ are as defined above, and isolating the compound of Formula-13;

k) reacting the isolated compound of Formula-13 with an inorganic or organic acid in an ether solvent, ester solvent, polar aprotic solvent, ketone solvent, alcoholic solvent, hydrocarbon solvent, chloro solvent, water, or a mixture thereof to provide the compound of Formula-1; and l) purifying the compound of Formula-1 in a solvent to provide the compound of Formula-1 having purity greater than 99.00% by HPLC.

2. The process of claim 1, wherein:

i) in step a), the base is an alkali metal hydroxide, alkali metal carbonate the solvent is selected from dibutylether, methyl tert-butyl ether, dioxane and tetrahydrofuran; and the acid is selected from paratoluene sulfonic acid, hydrochloric acid, oxalic acid and methane sulfonic acid;

ii) in step b), the base is selected from sodium hydroxide, potassium hydroxide and lithium hydroxide; the solvent is water; and the hydrocarbon solvent is selected from $C_5$-$C_{10}$ aliphatic hydrocarbons aromatic hydrocarbon solvents, and cyclohexane, or mixtures thereof;

iii) in step c), the resolving agent is L-proline methyl ester, or its salts, or R(+)-phenylethylamine; the solvent is selected from alcohol solvents, ester solvents, and ether solvents, or a mixture thereof; and the hydrocarbon solvent is selected from $C_5$-$C_{10}$ aliphatic hydrocarbons, aromatic hydrocarbon solvents and cyclohexane, or mixtures thereof iv) in step d), the amine is selected from monomethylamine, ethyl amine, n-propylamine, isopropylamine, n-butylamine, 2-butylamine, tertiary butyl amine, cyclohexyl amine, dicyclohexyl amine, benzyl amine and R-phenylethylamine;

v) in step f), the solvent is methanol, ethanol or isopropanol; the acid catalyst is selected from sulfuric acid, hydrochloric acid, thionyl chloride, methane sulfonic acid and paratoluene sulfonic acid; the hydrocarbon solvent is selected from $C_5$-$C_{10}$ aliphatic hydrocarbons, aromatic hydrocarbon solvents and cyclohexane, or mixtures thereof;

in step g), the solvent is methanol, ethanol, isopropanol, 2-butanol or mixtures thereof;

vii) in step h), the base is selected from alkali metal hydride, alkali metal carbonate, alkali metal hydroxide, alkali metal amide and alkoxide; and the solvent is a polar aprotic solvent or a ketone solvent;

viii) in step i), the base is an alkali metal hydroxide or an alkali metal carbonate; the solvent is selected from polar solvent, alcohol solvent and ether solvent, or a mixture thereof; and the ester solvent is selected from ethyl acetate, methyl acetate and propyl acetate;

ix) in step j), the amine is selected from monomethylamine, ethyl amine, n-propylamine, isopropylamine, n-butylamine, 2-butylamine, tertiary butyl amine, cyclohexyl amine, dicyclohexyl amine, benzyl amine and R-phenylethylamine; or x) in step 1), solvent is methanol, ethanol, isopropanol, butanol or mixtures thereof.

3. A process for the purification of a compound having the following structural formula:

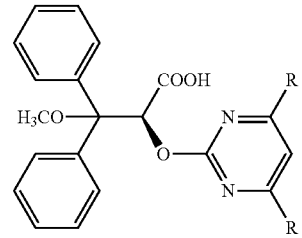

Formula-1 wherein R is methyl or methoxy;

the process comprising:

a) dissolving the compound of Formula-1 in alcohol solvent or water or a mixture thereof by heating to reflux, thereby forming a solution;

b) filtering the solution to remove extraneous matter;

c) cooling the filtered solution and stirring to yield a precipitated solid;

d) filtering the precipitated solid and washing the filtered solid with alcohol solvent or water or a mixture thereof; and e) drying the filtered solid to obtain purified compound of Formula-1.

4. The process according to claim 1, wherein the compound of Formula-1 is represented by the following structural formula:

5. The process according to claim 1, wherein the compound of Formula-1 is represented by the following structural formula:

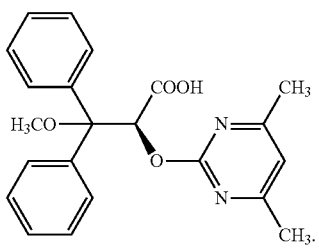 [SMILES: COC(c1ccccc1)(c1ccccc1)[C@H](Oc1nc(C)cc(C)n1)C(=O)O]

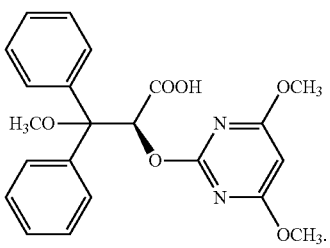 [SMILES: COc1cc(OC)nc(O[C@H](C(=O)O)C(OC)(c2ccccc2)c2ccccc2)n1]

6. The process according to claim 1, wherein R is methyl; and the solvent in step h) is a ketone solvent or polar aprotic solvent, or mixture thereof.

7. The process according to claim 6, wherein in step h), the base is selected from an alkali metal carbonate, alkali metal hydroxide and alkali metal amide; the polar aprotic solvent is selected from dimethyl formamide, dimethylacetamide, and dimethyl sulfoxide; and the ketone solvent is selected from acetone, methyl ethyl ketone, methyl isopropyl ketone and methyl isobutyl ketone.

8. A process for the preparation of pure compound of Formula-1a

Formula-1a

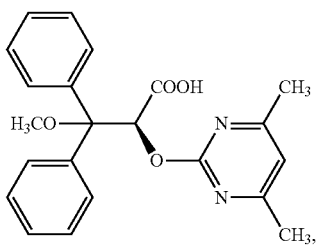

the process comprising:
a) reacting benzophenone with methyl chloroacetate in presence of sodium methoxide in tetrahydrofuran to provide 3,3-diphenyloxirane-2-carboxylic acid methyl ester, which is treated in-situ with methanol in presence of paratoluene sulfonic acid to provide 2-hydroxy-3-methoxy-3,3-diphenylpropionic acid methyl ester compound of Formula-5a;
b) hydrolyzing the compound of Formula-5a with aqueous sodium hydroxide followed by crystallization from cyclohexane, to provide 2-hydroxy-3-methoxy-3,3-diphenylpropionic acid compound of Formula-6;
c) resolving the compound of Formula-6 by treating with L-proline methyl ester in methyl tert-butyl ether followed by crystallization from toluene, to provide (S)-2-hydroxy-3-methoxy-3,3-diphenylpropionic acid compound of Formula-7;
d) reacting the compound of Formula-7 with R(+)-phenylethylamine in ethyl acetate to provide R(+)-phenylethylamine salt of (s)-2-hydroxy-3-methoxy-3,3-diphenylpropionic acid compound of Formula-11a;
e) treating the compound of Formula-11a with aqueous hydrochloric acid to provide the compound of formula-7;
f) reacting the compound of formula-7 from step e) with methanol and paratoluene sulfonic acid followed by isolation from cyclohexane, to provide (S)-2-hydroxy-3-methoxy-3,3-diphenylpropionic acid methyl ester compound of Formula-8a;
g) crystallizing the compound of Formula-8a using 2-butanol to provide crystalline compound of Formula-8a;
h) reacting the crystalline compound of Formula-8a with 4,6-dimethyl-2-(methylsulphonyl)pyrimidine in presence of potassium carbonate in dimethylformamide to provide (+)-(2S)-2-[(4,6-dimethylpyrimidin-2-yl)oxy]-3-methoxy-3,3-diphenylpropanoic acid methyl ester compound of Formula-10a;
i) hydrolyzing the compound of Formula-10a with aqueous sodium hydroxide in dioxane followed by isolation using ethyl acetate, to provide the compound of Formula-1a;
j) reacting the compound of Formula-1a with monomethyl amine in ethyl acetate to provide compound of Formula-13a Formula-13a

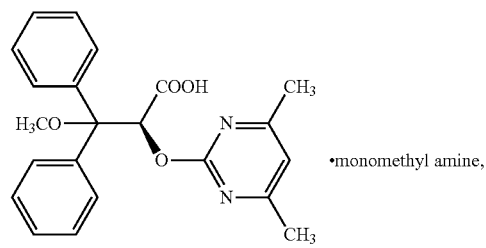

k) reacting the compound of Formula-13a with hydrochloric acid in water to provide the compound of Formula-1a; and
l) purifying the compound of Formula-1a in isopropyl alcohol to provide compound of Formula-1a having purity greater than 99.00% by HPLC.

9. A process for the preparation of crystalline form-M of a compound having the following structure:

Formula-1a

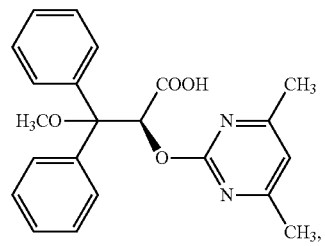

and characterized by any one of the following:
i) X-ray diffractogram having peaks at about 7.54, 8.86, 12.29, 13.06, 14.13, 15.18, 18.2, 20.55, 22.91, 24.26, 26.86, 28.9, 36.54 and 40.45±0.2 degrees two theta; or
ii) IR spectrum having peaks at about 3057.6, 2965.8, 1752.6, 1559.2, 1493.2, 1446.0, 1406.5, 1379.8, 1313.4, 1192.7, 1075.5, 1001.7, 877.0, 701.1 and 611.9 cm$^{-1}$, the process comprising:
a) dissolving the compound of Formula-1a in an alcoholic solvent or water or mixtures thereof at reflux temperature;
b) stirring the reaction mixture at reflux;
c) cooling the reaction mixture, thereby forming a precipitate;
d) filtering the precipitate and washing the filtered precipitate with alcoholic solvents or water or mixtures thereof; and
e) drying the filtered solid to get the crystalline form-M of the compound of Formula-1a.

10. A process for the preparation of crystalline form-M of a compound having the following structural formula:

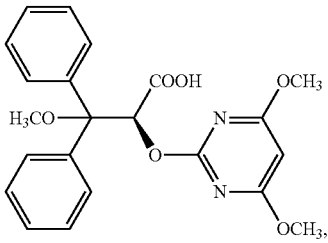

Formula-1b and characterized by any one of the following:
i) X-ray diffractogram having peaks at about 5.02, 11.25, 13.89, 16.28, 19.3, 20.88, 22.72, 22.86, 24.11, 28.54, 30.23 and 33.72±0.2 degrees two theta; or
ii) IR spectrum having peaks at about 3118.2, 3004.6, 2963.5, 2835.9, 1754.3, 1593.7, 1486.2, 1447.1, 1316.8, 1218.5, 1130.5, 1094.5, 1072.3, 990.9, 825.1, 754.1, 703.2, 630.9 and 594.9 cm$^{-1}$;

the process comprising:
a) dissolving the compound of Formula-1b in an alcoholic solvent or water or mixtures thereof at reflux temperature;
b) stirring the reaction mixture at reflux;
c) cooling the reaction mixture, thereby forming a precipitate;
d) filtering the precipitate and washing the filtered precipitate with an alcoholic solvent or water or mixtures thereof; and
e) drying the filtered precipitate to get the crystalline form-M of the compound of Formula-1b.

* * * * *